(12) United States Patent
Nemirovsky et al.

(10) Patent No.: US 11,079,318 B2
(45) Date of Patent: Aug. 3, 2021

(54) GAS SENSING DEVICE AND A METHOD FOR SENSING GAS

(71) Applicants: TODOS TECHNOLOGIES LTD., Airport City (IL); TECHNION RESEARCH AND DEVELOPEMENT FOUNDATION LTD., Haifa (IL)

(72) Inventors: Yael Nemirovsky, Haifa (IL); Amikam Nemirovsky, Haifa (IL)

(73) Assignees: TODOS TECHNOLOGIES LTD., Airport City (IL); TECHNION RESEARCH AND DEVELOPMENT FOUNDATION LTD., Haifa (IL)

(*) Notice: Subject to any disclaimer, the term of this patent is extended or adjusted under 35 U.S.C. 154(b) by 354 days.

(21) Appl. No.: 16/081,953

(22) PCT Filed: Mar. 9, 2017

(86) PCT No.: PCT/IL2017/050309
§ 371 (c)(1),
(2) Date: Sep. 4, 2018

(87) PCT Pub. No.: WO2017/203507
PCT Pub. Date: Nov. 30, 2017

(65) Prior Publication Data
US 2020/0292443 A1   Sep. 17, 2020

Related U.S. Application Data

(60) Provisional application No. 62/339,985, filed on May 23, 2016, provisional application No. 62/306,096, filed on Mar. 10, 2016.

(51) Int. Cl.
*G01N 21/31* (2006.01)
*G01N 33/00* (2006.01)

(52) U.S. Cl.
CPC ......... *G01N 21/31* (2013.01); *G01N 33/0027* (2013.01); *G01N 2201/0221* (2013.01)

(58) Field of Classification Search
CPC ............... G01N 21/31; G01N 33/0027; G01N 2201/0221; G01N 2021/3166; G01N 2021/3531; G01N 21/314; G01N 21/3504
See application file for complete search history.

(56) References Cited

U.S. PATENT DOCUMENTS 4,678,332 A * 7/1987 Rock .................... G01J 3/02
                                                    250/338.5
5,650,624 A * 7/1997 Wong ................ G01N 21/3504
                                                    250/338.5

(Continued)

OTHER PUBLICATIONS

Search Report PCT/IL2017/050309 dated Jul. 22, 2017.

*Primary Examiner* — Mohamed K Amara
(74) *Attorney, Agent, or Firm* — Reches Patent

(57) ABSTRACT

There is provided a gas sensing device for sensing a certain gas that is associated with a certain spectral band, the gas sensing device may include a passive gas sensor that is configured to generate passive gas sensor detection signals that are responsive to the certain spectral band; a passive dummy sensor that is configured to generate passive dummy sensor detection signals that are indifferent to the certain spectral hand; and at least one circuit that is configured to detect a presence or absence of the certain gas within a certain volume that is located within the fields of view of the passive gas sensor and the passive dummy sensor based on a comparison between the passive gas sensor detection signals and the passive dummy sensor detection signals.

22 Claims, 8 Drawing Sheets

(56) References Cited

U.S. PATENT DOCUMENTS

| | | | | |
|---|---|---|---|---|
| 5,721,430 A * | 2/1998 | Wong | G01N 21/3518 | 250/339.13 |
| 5,989,398 A * | 11/1999 | Young | G01N 25/30 | 204/408 |
| 7,176,460 B1 * | 2/2007 | Wong | G01N 21/3504 | 250/336.1 |
| 8,193,496 B2 * | 6/2012 | Furry | G01N 33/0036 | 250/330 |
| 9,513,204 B2 * | 12/2016 | Paul | G01N 15/06 | |
| 10,151,744 B2 * | 12/2018 | Hok | G01N 21/3504 | |
| 10,768,153 B2 * | 9/2020 | Nemirovsky | G01N 33/0031 | |
| 2002/0011568 A1 | 1/2002 | Diekmann | | |
| 2002/0122314 A1 | 9/2002 | Kojima | | |
| 2006/0133960 A1 * | 6/2006 | Ahmad | A61B 5/083 | 422/83 |
| 2008/0056946 A1 * | 3/2008 | Ahmad | G01N 21/71 | 422/68.1 |
| 2008/0216567 A1 * | 9/2008 | Breed | B60N 2/888 | 73/146.5 |
| 2009/0046538 A1 * | 2/2009 | Breed | B60R 25/102 | 367/93 |
| 2009/0126460 A1 * | 5/2009 | Gardner | G01N 27/14 | 73/31.06 |
| 2010/0079282 A1 * | 4/2010 | Icove | G01K 11/006 | 340/561 |
| 2010/0207754 A1 * | 8/2010 | Shostak | B60C 23/0494 | 340/450 |
| 2010/0258728 A1 | 10/2010 | Wong | | |
| 2012/0031984 A1 * | 2/2012 | Feldmeier | F24F 11/30 | 236/49.3 |
| 2015/0316472 A1 * | 11/2015 | Yon | G08B 21/16 | 356/437 |
| 2016/0267769 A1 * | 9/2016 | Rokhsaz | H01Q 9/04 | |
| 2016/0274077 A1 * | 9/2016 | Perkins | G01J 3/12 | |

* cited by examiner

GAS SENSING DEVICE AND A METHOD FOR SENSING GAS

CROSS REFERENCE

This patent application claims priority from U.S. provisional patent 62/306,096 filing date Mar. 10 2016 and from U.S. provisional patent 62/339,985 filing date May 23 2016, both incorporated herein in their entirety.

BACKGROUND OF THE INVENTION

There is a growing need to sense gas in a cost effective and reliable manner.

SUMMARY

Methods, gas sensing devices as illustrated in the specification and/or the claims.

A gas sensing device for sensing a certain gas that may be associated with a certain spectral band, the gas sensing device may include:
a passive gas sensor that may be configured to generate passive gas sensor detection signals that may be responsive to the certain spectral band;
a passive dummy sensor that may be configured to generate passive dummy sensor detection signals that may be indifferent to the certain spectral band; and at least one circuit that may be configured to detect a presence or absence of the certain gas within a certain volume that may be located within the fields of view of the passive gas sensor and the passive dummy sensor based on a comparison between the passive gas sensor detection signals and the passive dummy sensor detection signals.

The at least one circuit may be configured to detect the presence or absence of the certain gas within the certain volume regardless of the optical length of each one of the passive gas sensor and the passive dummy sensor.

The at least one circuit may be configured to detect the presence or absence of the certain gas within the certain volume based on an optical length of each one of the passive gas sensor and the passive dummy sensor.

The at least one circuit may be configured to receive information about the optical length.

The at least one circuit may be configured to detect the presence or absence of the certain gas within the certain volume based, at least on ambient temperatures.

The at least one circuit may be configured to detect the presence or absence of the certain gas within the certain volume based on comparisons between passive gas sensor detection signals obtained during multiple measurements and passive dummy sensor detection signals obtained during the multiple measurements.

The multiple measurements may include a first measurement and a second measurement; wherein the first measurement was taken when the gas sensing device was positioned at a first position in which the passive gas sensor has a first optical length; wherein the second measurement was taken when the gas sensing device was positioned at a second position in which the passive gas sensor has a second optical length that differs by a known difference from the first optical length.

The at least one circuit may be configured to detect the presence or the absence of the certain gas within the certain volume based on the known difference, a first difference between passive gas sensor detection signals obtained during the first measurement and passive dummy sensor detection signals obtained during the first measurement, and a second difference between passive gas sensor detection signals obtained during the second measurement and passive dummy sensor detection signals obtained during the second measurement.

The at least one circuit may be configured to detect the presence or the absence of the certain gas within the certain volume based on an absolute value of a ratio between the second difference and the first difference.

The at least one circuit may be configured to detect a concentration of the certain gas within the certain volume by: dividing (a) the absolute value of the ratio between the second difference and the first difference, by (b) a product of the known difference multiplied by a gas absorption coefficient of the certain gas at a wavelength of detection of the passive gas sensor.

The at least one circuit may include a man machine interface for outputting instructing for positioning the gas sensing device at the first position and for outputting instructions for positioning the gas sensing device at the second position.

The first position may be on a floor of a room and facing a ceiling and wherein the second position may be on a head of a user and facing the ceiling.

The at least one circuit s configured to calculate the second position.

The gas sensing device may be a smartphone.

There may be provided a method for sensing a certain gas that may be associated with a certain spectral band, the method may include generating, by a passive gas sensor of a gas sensing device, passive gas sensor detection signals that may be responsive to the certain spectral band; generating, by a passive dummy sensor of a gas sensing device, passive dummy sensor detection signals that may be indifferent to the certain spectral band; and detecting, by at least one circuit, a presence or absence of the certain gas within a certain volume that may be located within the fields of view of the passive gas sensor and the passive dummy sensor based on a comparison between the passive gas sensor detection signals and the passive dummy sensor detection signals.

The method may include detecting the presence or absence of the certain gas within the certain volume regardless of the optical length of each one of the passive gas sensor and the passive dummy sensor.

The method may include detecting the presence or absence of the certain gas within the certain volume based on an optical length of each one of the passive gas sensor and the passive dummy sensor.

The method may include receiving information about the optical length.

The method may include detecting the presence or absence of the certain gas within the certain volume based, at least on ambient temperatures.

The method may include detecting the presence or absence of the certain gas within the certain volume based on comparisons between passive gas sensor detection signals obtained during multiple measurements and passive dummy sensor detection signals obtained during the multiple measurements.

The multiple measurements may include a first measurement and a second measurement; wherein the first measurement was taken when the gas sensing device was positioned at a first position in which the passive gas sensor has a first optical length; wherein the second measurement was taken when the gas sensing device was positioned at a second position in which the passive gas sensor has a second optical length that differs by a known difference from the first optical length.

The method may include detecting the presence or the absence of the certain gas within the certain volume based on the known difference, a first difference between passive gas sensor detection signals obtained during the first measurement and passive dummy sensor detection signals obtained during the first measurement, and a second difference between passive gas sensor detection signals obtained during the second measurement and passive dummy sensor detection signals obtained during the second measurement.

The method may include detecting the presence or the absence of the certain gas within the certain volume based on an absolute value of a ratio between the second difference and the first difference.

The method may include detecting a concentration of the certain gas within the certain volume by: dividing (a) the absolute value of the ratio between the second difference and the first difference, by (b) a product of the known difference multiplied by a gas absorption coefficient of the certain gas at a wavelength of detection of the passive gas sensor.

The method may include outputting instructions for positioning the gas sensing device at the first position and for outputting instructions for positioning the gas sensing device at the second position.

The method wherein the first position may be on a floor of a room and facing a ceiling and wherein the second position may be on a head of a user and facing the ceiling.

The method may include calculating the second position.

The gas sensing device may be a smartphone.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
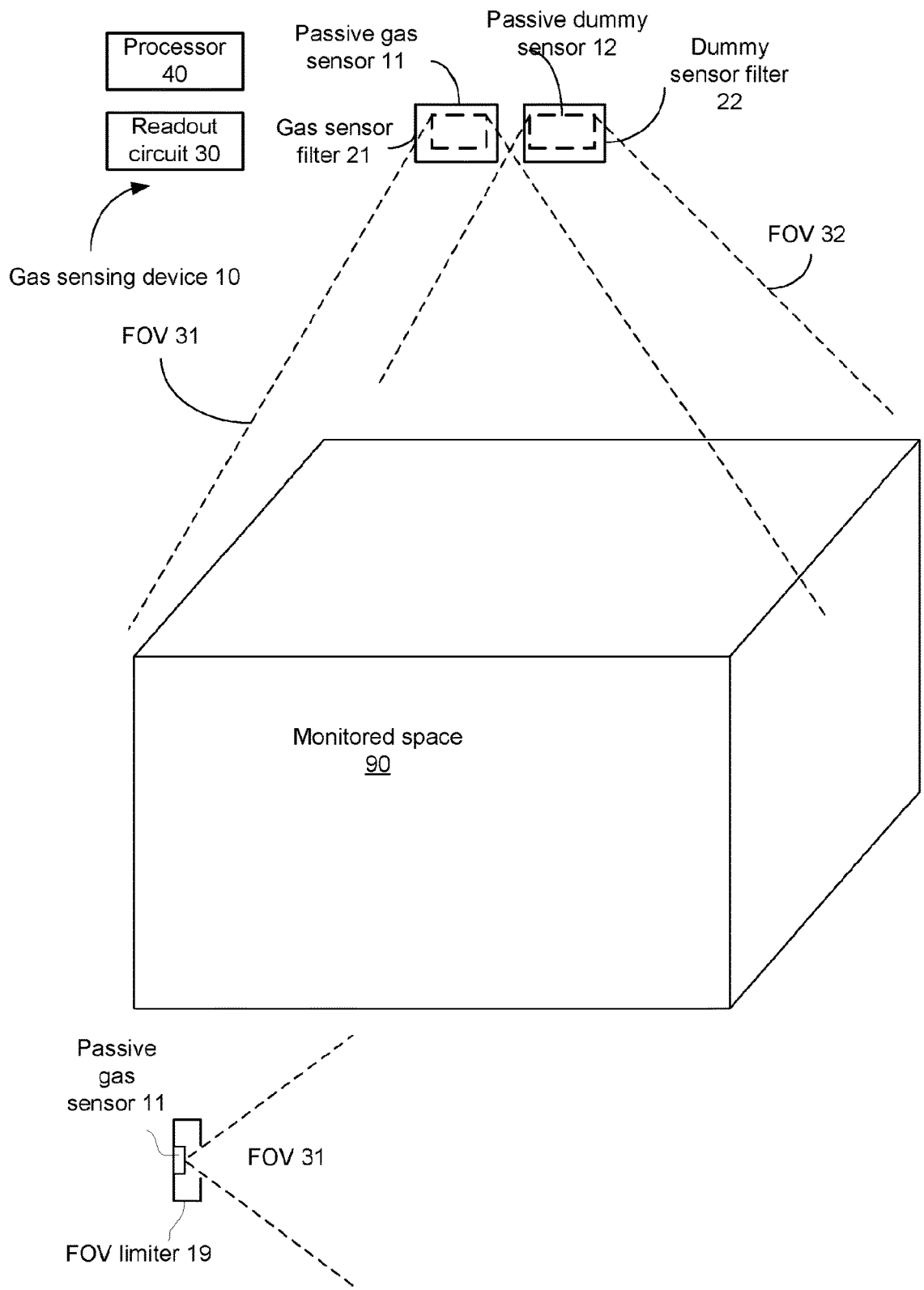
FIGS. 1-5 illustrate a gas sensing device and portions of said gas sensing device according to various embodiments of the invention.

It will be appreciated that for simplicity and clarity of illustration, elements shown in the Figures have not necessarily been drawn to scale. For example, the dimensions of some of the elements may be exaggerated relative to other elements for clarity. Further, where considered appropriate, reference numerals may be repeated among the Figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a gas sensing device capable of executing the method.

The term "comprising" is synonymous with (means the same thing as) "including," "containing" or "having" and is inclusive or open-ended and does not exclude additional, unrecited elements or method steps.

The term "consisting" is a closed (only includes exactly what is stated) and excludes any additional, unrecited elements or method steps.

The term "consisting essentially of" limits the scope to specified materials or steps and those that do not materially affect the basic and novel characteristics.

In the claims and specification any reference to the term "comprising" (or "including" or "containing") should be applied mutatis mutandis to the term "consisting" and should be applied mutatis mutandis to the phrase "consisting essentially of".

In the claims and specification any reference to the term "consisting" should be applied mutatis mutandis to the term "comprising" and should be applied mutatis mutandis to the phrase "consisting essentially of".

In the claims and specification any reference to the phrase "consisting essentially of" should be applied mutatis mutandis to the term "comprising" and should be applied mutatis mutandis to the term "consisting".

The terms "module" and "device" are used in an interchangeable manner.

Any reference in the specification to a gas sensing device should be applied mutatis mutandis to a method that may be executed by the gas sensing device.

There is a provided a passive non-dispersive (NDIR) sensor module (hereinafter-gas sensing device). The gas sensing device may include a passive gas sensor and a passive dummy sensor. The gas sensing device is capable of sensing one or more gases. Few examples of sensed gasses include $CO_2$, $C_2H_2$, $NH_3$ and many more.

In contrary to active NDIR gas sensors—the suggested gas sensing device does not require an infrared radiation source that operates at relatively high temperature and does not require high sensitivity (and usually expensive) infrared sensors.

Accordingly—the gas sensing device may be cheap, of small size and of low power consumption.

The passive gas sensor and the passive dummy sensor may be or may include, for example, a TMOS sensor such as the sensor illustrated in U.S. Pat. No. 7,489,024 which is incorporated herein by reference.

The passive gas sensor and the passive dummy sensor may be ideally identical to each other—or at least have known responses to radiations emitted on these sensors. If there are differences between the known responses—these differences are taken into account (compensated) during the detection process.

The passive gas sensor and the passive dummy sensor are positioned to face a monitored space that may include a certain volume.

The monitored space may be, for example, a room, an interior of a car, an open space, multiple rooms and/or corridors, and the like. The certain volume (of the monitored space) may be one cubic meter, less than one cubic meter or may exceed one cubic meter.

In many scenarios, the certain volume of the monitored space may exceed ten cubic meters.

The line of sight of each one of the passive gas sensor and the passive dummy sensor may be less than a meter, a meter or more than a meter. The field of view of the passive gas sensor and the field of view of the passive dummy sensor should cover the monitored space.

A certain gas may be associated with a certain spectral band. Accordingly—when the certain gas is present within the monitored space the spectral response of the monitored space to radiation may change in that certain spectral band.

The passive gas sensor may be configured to be responsive to the certain spectral band. Accordingly—the lack of a certain gas within the monitored space or the presence of the certain gas within the monitored space are expected to result in different passive gas sensor detection signals.

The passive dummy sensor may ignore the certain spectral band. Accordingly—the passive dummy sensor is configured to be indifferent to the lack or the presence of the certain gas within the monitored space.

Appropriate filters (one for rejecting signals of the certain spectral band and another for passing signals within the certain spectral band) can be positioned before the passive dummy sensor and the passive gas sensor, respectively. It is noted that the filters may be integrated with the gas and passive dummy sensors.

Different gases may be sensed by using passive gas sensors that are configured to sense signals in different spectral bands that are associated with the different gases. If there are N (N being a positive integer that exceeds one) different gases that are associated with N different spectral bands than there may be N passive gas sensor and between 1 and N (for example N−1) passive dummy sensors. Each passive dummy sensor may be configured to reject signals from all of the N different spectral bands.

A difference between detection signals provided from a passive gas sensor and a corresponding passive dummy sensor may provide an indication about a presence of a gas.

A corresponding passive dummy sensor may be tuned to ignore the gas that is sensed by the corresponding passive gas sensor).

The difference may be calculated in the analog domain, in the digital domain, by the readout circuit, by a processor of the gas sensing device, by a processor that does not belong to the gas sensing device, and the like.

A detection of a certain gas within the monitored volume may be responsive to the outputs of the passive gas sensor and the passive dummy sensor as well as other parameters such as the dimensions (volume, length of line of sight of the passive gas sensor and/or the passive dummy sensor) which may be fed to a processor.

For example, the certain gas may absorb and emit radiation at certain discrete wavelengths (certain spectral band). This produces a unique spectrum for each gas species. Moreover, the degree of attenuation of the spectrum depends on the concentration, assuming the optical length (line of sight of the passive gas sensor and/or the passive dummy sensor) is known.

A processor may be fed with the line of sight length in advance, after the installation of the gas sensing device, and the like. Accordingly, in principle, the selectivity and concentration may be determined in high accuracy. The absorption or transmission spectrum of the gases are by now well documented in the open literature. See for example www.spectralcalc.com. The software provides the attenuation vs concentration as well.

FIG. 1 illustrates a gas sensing device 10 according to an embodiment of the invention.

Gas sensing device 10 includes passive gas sensor 11, gas sensor filter 21, dummy sensor filter 22, readout circuit 30 and processor 40. The monitored space 90 is within the field of view (FOV) 31 of the passive gas sensor and within the field of view (FOV) 32 of the passive dummy sensor 12.

The passive gas sensor may be followed by optics or may not be followed by optics.

The passive gas sensor 11 may be followed by a FOV limiter 19 that has one or more apertures (formed in an opaque material) that define FOV 31. The FOV limiter 19 may be shaped as a bot that has an aperture that is positioned in front of the passive gas sensor.

The same FOV limiter may be provided for the passive dummy sensor.

Figure 2:
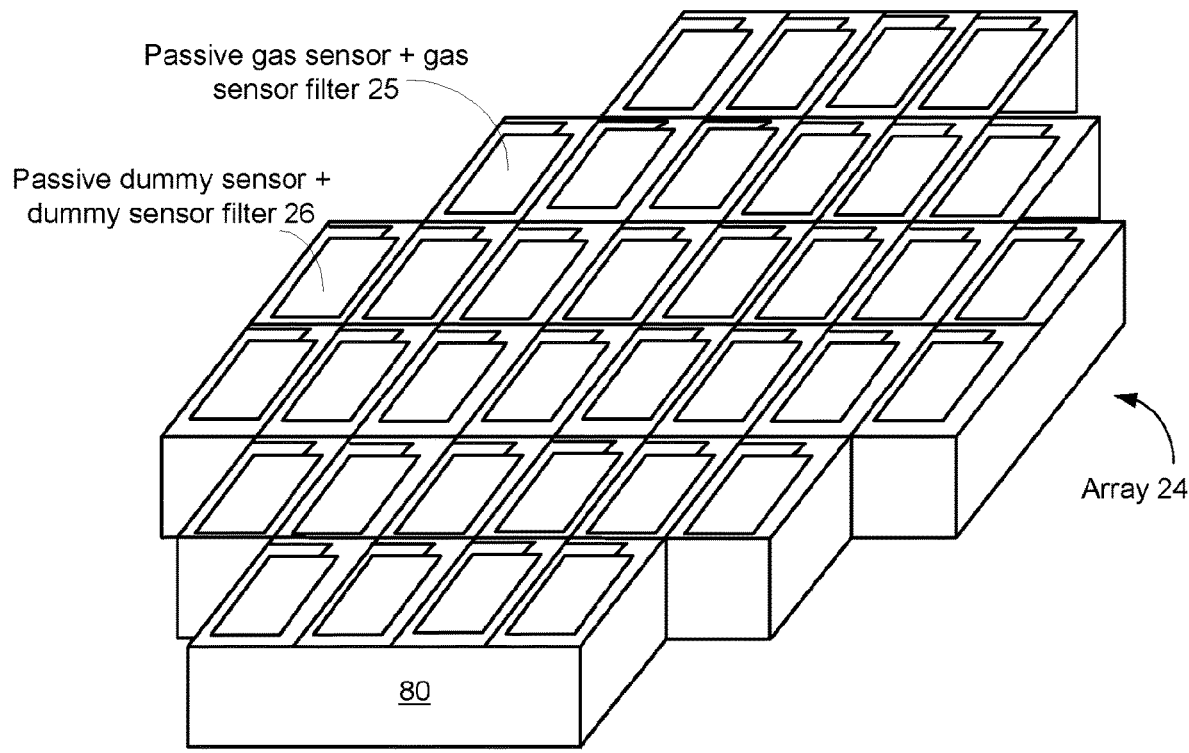

FIG. 2 illustrates any array of sensors and filters such as passive gas sensor and gas sensor filter (collectively denoted 25) and passive dummy sensor and dummy sensor filter (collectively denoted 26) that are suspended and are connected by arms to frame 80.

The array may include one or more passive gas sensors that are configured to sense one or more gases. There may be any relationships between the number and/or location of the as passive gas sensor and gas sensor filter and the number and/or locations of the passive dummy sensor and dummy sensor filter.

For example—there may be N passive gas sensor and gas sensor filters and between 1 to N−1 passive dummy sensor and dummy sensor filters.

The passive gas sensor and gas sensor filter may be arranged in one or more groups—for example in rows, in columns, in two dimensional grids and the like. The same applies to the passive dummy sensors.

Figure 3:
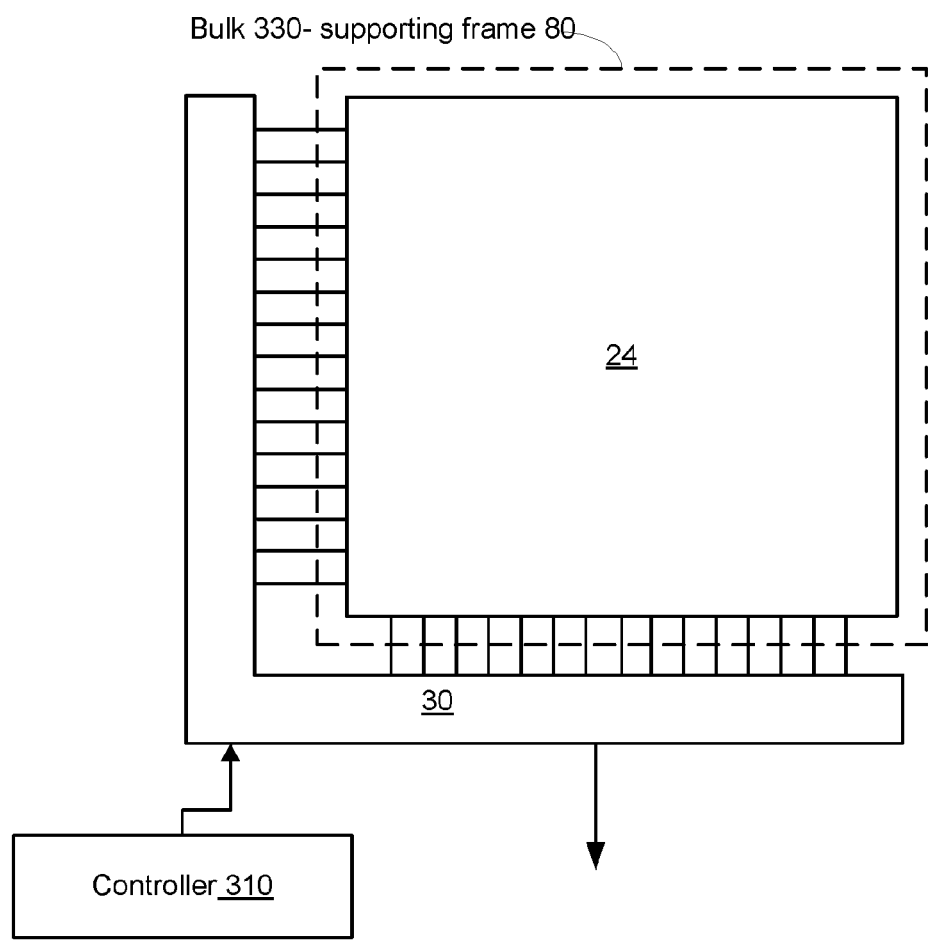

FIG. 3 illustrates a readout circuit 30, an array 24 of passive gas sensors and passive dummy sensors, and a controller 310 for controlling the readout circuit 30. The controlling may include selecting which passive gas sensor and/or passive dummy sensor of the array to be read at a given point of time by using row and/or column signals.

Figure 4:
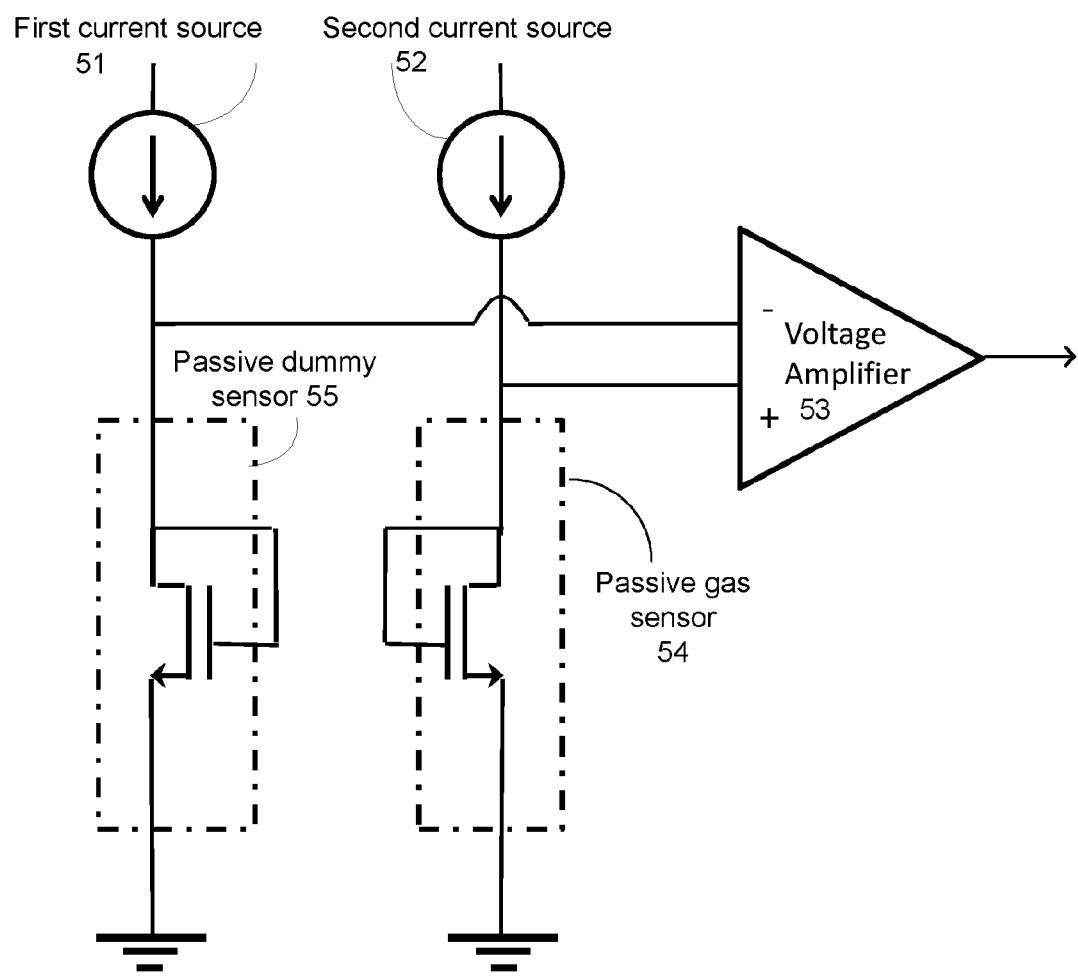
Figure 5:
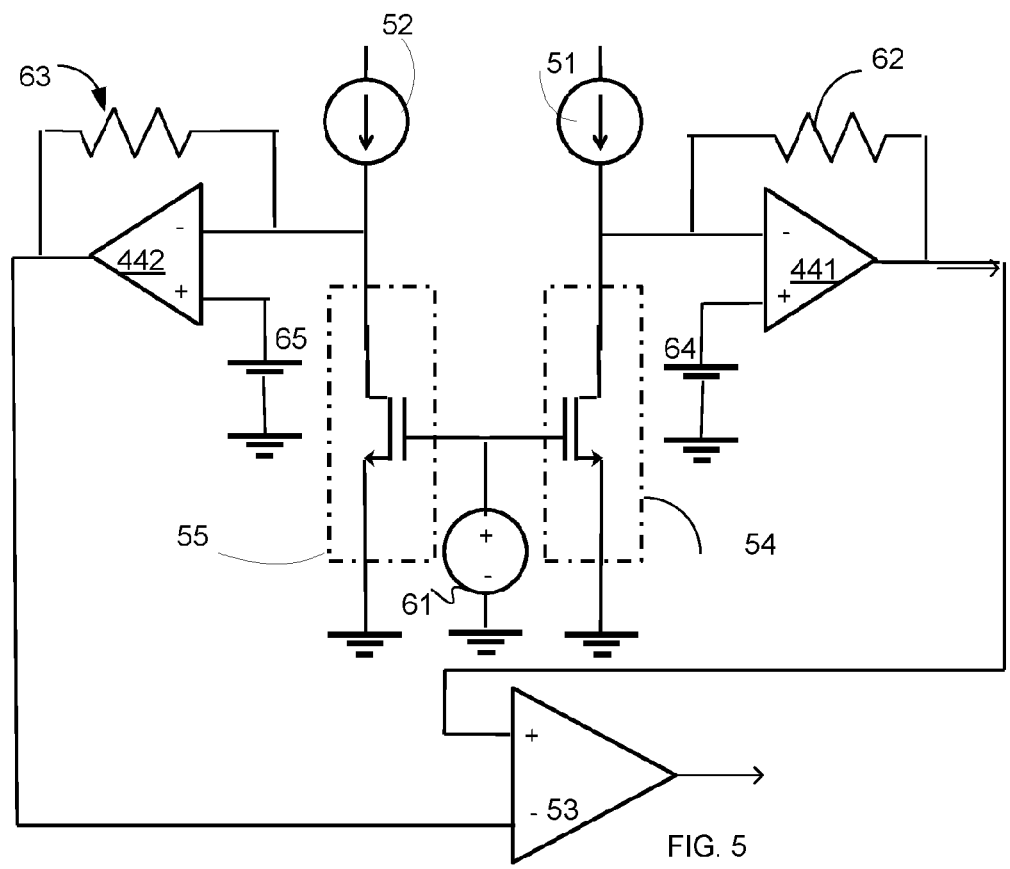

FIG. 4 and FIG. 5 illustrate passive gas sensor, passive dummy sensor and analog domain processing circuits—such as current differential sensing circuits of FIG. 4 and voltage differential sensing circuits of FIG. 5.

FIG. 4 illustrates a passive gas sensor 54, a passive dummy sensor 55, first and second current sources 51 and 52 and a voltage amplifier 53 according to an embodiment of the invention.

Each one of passive gas sensor 54 and passive dummy sensor 55 has a CMOS transistor that is coupled as a diode but may also be operated with three terminals. A passive gas sensor detection signal is outputted by passive gas sensor 54 and is a voltage detection signal. The passive gas sensor detection signal reflects the gas sensed by the passive gas sensor. A passive dummy sensor detection signal is generated by the passive dummy sensor 55—and should be indifferent to the presence or absence of the gas sensed by the passive gas sensor.

The passive gas sensor detection signal is fed to a non-inverting input of voltage amplifier 53. The passive dummy sensor detection signal may be fed to an inverting input of voltage amplifier 53. Voltage amplifier 53 calculates the difference between the passive gas sensor detection signal and the passive dummy sensor detection signal.

First and second current sources 51 and 52 may belong to a signals source module that is coupled to (or included in) the readout circuit 30 of FIG. 3 and are provided, via an interfacing module (such as the readout circuit) to passive gas sensor 54 and passive dummy sensor 55 respectively.

Voltage amplifier 53 may belong to readout circuit 30 of FIG. 3. Voltage amplifier 53 may receive the passive gas sensor detection signal and/or the passive dummy sensor detection signal via an interfacing module.

FIG. 5 illustrates a passive gas sensor 54, a passive dummy sensor 55, current sources 51 and 52, bias source 61, and first and second voltage sources 64 and 65, first and second trans-impedance amplifiers 441 and 442, a voltage amplifier 53 and feedback resistors 62 and 63 according to an embodiment of the invention.

In FIG. 5 the passive gas sensor detection signal is a current detection signal and the passive dummy sensor detection signals is a reference current signal.

Bias source 61 provides a gate bias voltage to the gates of the CMOS transistors of passive gas sensor 54 and passive dummy sensor 55.

First trans-impedance amplifier 441 receives at its non-inverting input a bias voltage from voltage source 64.

A first current that is a difference between a first fixed current (from first current source 51) and the passive gas sensor detection signal is fed to an inverting input of first trans-impedance amplifier 441 and to first feedback resistor 62 to provide a first intermediate voltage that is then fed to a non-inverting input of voltage amplifier 443.

A second current that is a difference between a second fixed current (from second current source 52) and the passive dummy sensor detection signal is fed to an inverting input of second trans-impedance amplifier 442 and to second feedback resistor 63 to provide a second intermediate voltage that is then fed to an inverting input of voltage amplifier 443.

Voltage amplifier 443 outputs an output signal that represents the difference between the passive dummy sensor detection signal and the passive gas sensor detection signal—which indicates the presence or absence of gas.

The passive gas sensor may sense the room and its signal depends on the average temperature of the ceiling and walls. The blackbody radiation that the passive gas sensor (such as a TMOS) passively senses may be attenuated by the gas, which needs to be detected. The degree of attenuation is determined by the concentration of the gas (normally expressed in ppm) as well as the length of the optical path. The attenuation follows Beer's law and is determined by what is known as the overall mass path.

In the case of the TMOS, the available optical path may be of the order of several meters (corresponding to the dimensions of a typical room).

The passive gas sensor and the dummy gas sensor may be preceded by filters and may not be preceded by additional optics.

The passive dummy sensor sensing the electric signal produced at spectral band that does not include the one corresponding to the gas to be sensed. The electrical signal is denoted by $I_b$.

The passive gas sensor may be a TMOS with a filter corresponding to the spectral band of the sensed gas.

The detection pf the certain gas is based on multiple measurements

During the first measurement, the device that includes the gas and passive dummy sensors (for example a smartphone) may be positioned on a head of the user and looking to ceiling.

The electrical signal sensed by the passive gas sensor is denoted by $I_{s1}$. The optical path is the distance between floor to ceiling denoted by L minus the person height denoted by h.

During the second measurement, the device is placed on the floor (same spot—directly below the spot of the first measurement) looking to ceiling. The electrical signal of the passive gas sensor is denoted by $I_{s2}$.

The optical path is the distance between floor to ceiling denoted by L.

By taking the ratio of the two measurements, the emissivity and the Planck radiation law expressing the blackbody radiation of the ceiling are canceled. Hence, there is no need to determine the temperature accurately.

Accordingly, and assuming that the passive dummy sensor readings are the same during the two measurements ($I_{b1}=I_{b2}$) then $$\frac{I_{s2} - I_b}{I_{s1} - I_b} = \frac{\varepsilon(\lambda_s) f(T, \lambda_s)}{\varepsilon(\lambda_s) f(T, \lambda_s)} \frac{\exp[-L\alpha C]}{\exp[-(L-h)\alpha C]} = \exp[-h\alpha C]$$

$$C = \frac{1}{h\alpha} \ln \left| \frac{I_{s2} - I_b}{I_{s1} - I_b} \right|$$

If there is a difference between the two measurements of the passive dummy sensor to provide $I_{b1}$ and $I_{b2}$, then:

$$C = \frac{1}{h\alpha} \ln \left| \frac{I_{s2} - I_{b2}}{I_{s1} - I_{b1}} \right|$$

The gas concentration C is determined by the person height H, the gas absorption coefficient α at the wavelength of detection, and the natural logarithm of the ratio between the 2 measurements.

The a of each gas at a specific wavelength is known and can be obtained from a variety of sources.

It should be noted that the height of a person is merely an example of a known difference between points of measurements. The mentioned above process may be applied on measurements taken from different locations of known spatial relationships-especially of known optical paths.

Known differences may be attributed to dimensions of a person (height or any known dimensions—such as the length of the arm, length of a foot, length of a head or any other organ). Know differences may be attributed to objects that are in the room—such as a height or weight or a length of a window, of a floor tile, of a furniture, of a door, and the like.

This approach is in particular suitable for measuring the quality of air indoors.

However, this approach can be extended to outdoors.

The suggested process may require two measurements with a known difference H between the optical path.

Adding more measurements from the same points or from at least one other point can provide yet more accurate results. For example—measurements from the same point may be averaged or otherwise processed to reduce noise.

By taking two consecutives measurements with the passive gas sensor and a with known significant distance of (for example at least one meter) between the two measurements, a gas sensing device can provide the concentration of many gases in the air.

It is noted that the mentioned above first and second measurements may be taken between any two points that are positioned at a known distance between them. For example, the first measurement may be taken when the device is positioned on a table, facing a certain object (wall, window, ceiling, floor) and the second measurement can be taken while the device is on the floor.

The suggested approach may be used for monitoring the breath of a person—by taking two measurements while the device is located at different distances from the mouth of the person. The gas sensing device may be equipped with a nozzle, pipe or another gas conduit for directing the gas from the mouth of the user towards the passive gas sensor and the passive dummy sensor of the gas sensing device.

Figure 6:
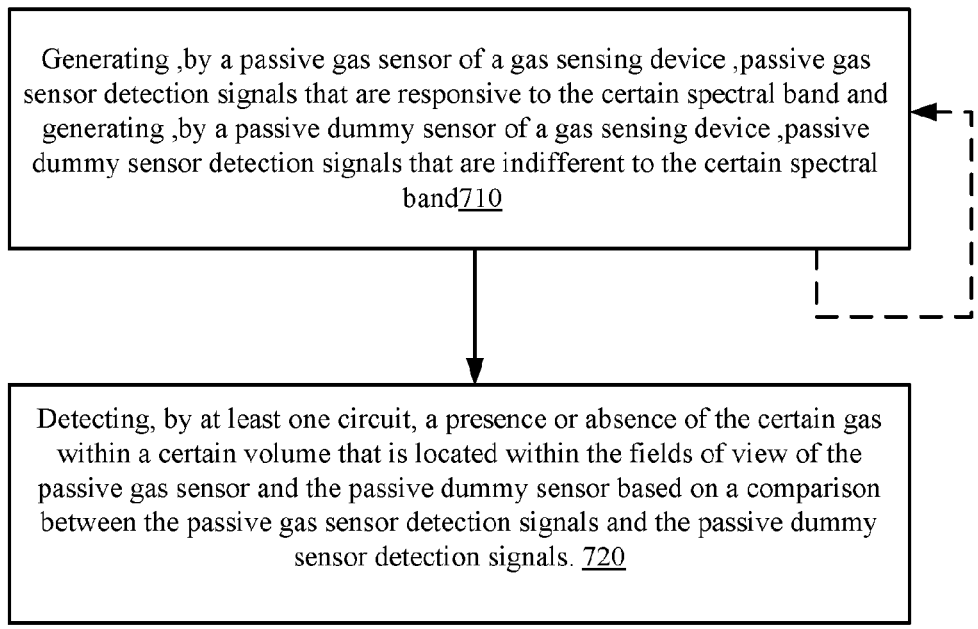
FIG. 6 illustrates a method according to an embodiment of the invention.

FIG. 6 illustrates method 700 according to an embodiment of the invention.

Method 700 may be provided for sensing a certain gas that is associated with a certain spectral band.

Method 700 may include performing one or more measurements. The one or more measurements may be taken when a gas sensing device is located in at least one location. If Q is a positive integer that exceeds one, then there may be Q measurements that are taken when the gas sensing device is positioned at one to Q different locations.

Each measurement may include generating (step 710), by a passive gas sensor of a gas sensing device, passive gas sensor detection signals that are responsive to the certain spectral band and generating, by a passive dummy sensor of a gas sensing device, passive dummy sensor detection signals that are indifferent to the certain spectral band.

One or more measurements may be followed by step 720 of detecting, by at least one circuit, a presence or absence of the certain gas within a certain volume that is located within the fields of view of the passive gas sensor and the passive dummy sensor based on a comparison between the passive gas sensor detection signals and the passive dummy sensor detection signals.

For example—if Q measurements are taken, step 720 may include between 1 and Q repetitions of step 720.

It should be noted that the detection of the presence or absence of the certain gas within the certain volume may or may not include detection of the concentration of the certain gas within the certain volume.

Step 720 may include at least one of the following:
a. Detecting the presence or absence of the certain gas within the certain volume regardless of the optical length of each one of the passive gas sensor and the passive dummy sensor.
b. Detecting the presence or absence of the certain gas within the certain volume based on an optical length of each one of the passive gas sensor and the passive dummy sensor.
c. Detecting the presence or absence of the certain gas within the certain volume based, at least on ambient temperatures.

Method 700 may also include receiving information about the optical length.

Method 700 may include performing multiple measurements when the gas sensing device is positioned at one or more locations. Step 720 may include detecting the presence or absence of the certain gas within the certain volume based on comparisons between passive gas sensor detection signals obtained during multiple measurements and passive dummy sensor detection signals obtained during the multiple measurements.

The multiple measurements may include a first measurement and a second measurement. The first measurement was taken when the gas sensing device was positioned at a first position in which the passive gas sensor has a first optical length. The second measurement was taken when the gas sensing device was positioned at a second position in which the passive gas sensor has a second optical length that differs by a known difference from the first optical length.

In this case, step 720 may include at least one out of:
a. Detecting the presence or the absence of the certain gas within the certain volume based on the known difference, a first difference between passive gas sensor detection signals obtained during the first measurement and passive dummy sensor detection signals obtained during the first measurement, and a second difference between passive gas sensor detection signals obtained during the second measurement and passive dummy sensor detection signals obtained during the second measurement
b. Detecting the presence or the absence of the certain gas within the certain volume based on an absolute value of a ratio between the second difference and the first difference.
c. Detecting a concentration of the certain gas within the certain volume by: dividing (a) the absolute value of the ratio between the second difference and the first difference, by (b) a product of the known difference multiplied by a gas absorption coefficient of the certain gas at a wavelength of detection of the passive gas sensor.

According to an embodiment of the invention the gas sensing device (or another device) may calculate the first and second positions (for example using location sensors, image sensors, accelerators, orientation sensors, gyroscopes and the like) in order to provide first and second positions that allow a known difference between the first and second optical lengths. For example—the gas sensing device (or another device) may calculate the second location based on the first location and the known difference.

The known difference may be set by a user of the gas sensing device, by a technician, by a manufacturer of the gas sensing device and the like.

The known difference may be large enough to provide adequate difference between the different measurements. For example—the difference may exceed 10 centimeters.

Method 700 may include outputting instructions for positioning the gas sensing device at the first position and for outputting instructions for positioning the gas sensing device at the second position.

These instructions may be human perceivable instructions (that can be heard, seen or otherwise sensed by a user) and/or may be sent to another device or unit (such as an earphone, a smartphone and the like) that will generate the human perceivable instructions.

Figure 7:
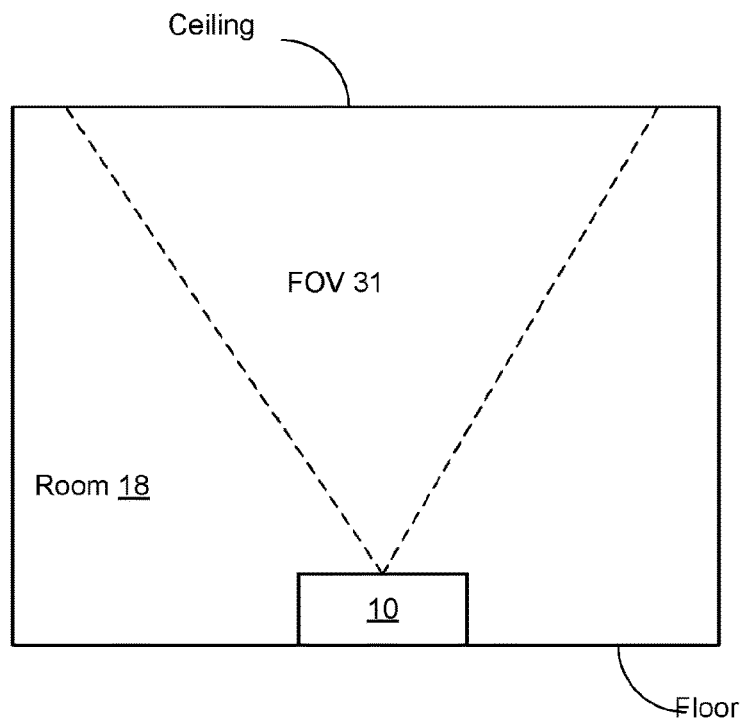
FIG. 7 illustrates two measurements according to an embodiment of the invention.
Figure 7:
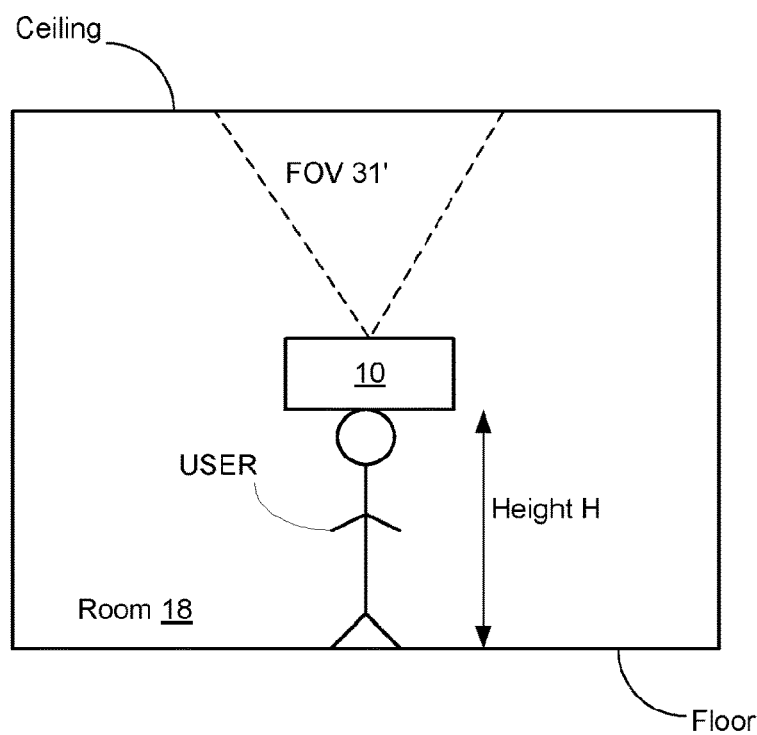

FIG. 7 illustrates a room 18 that has a ceiling and a floor and two measurements taken towards the ceiling—one with the gas sensing device is located on the floor and another measurement taken when the gas sensing device is on the head of the user—at height H. While the field of view (31 and 31') of the passive gas sensor may change—and "cover" different volumes within room 18—it may be assumed that the gas is evenly distributed in the room and/or that uneven distribution of the gas is known or estimated and may be taken into account.

Figure 8:
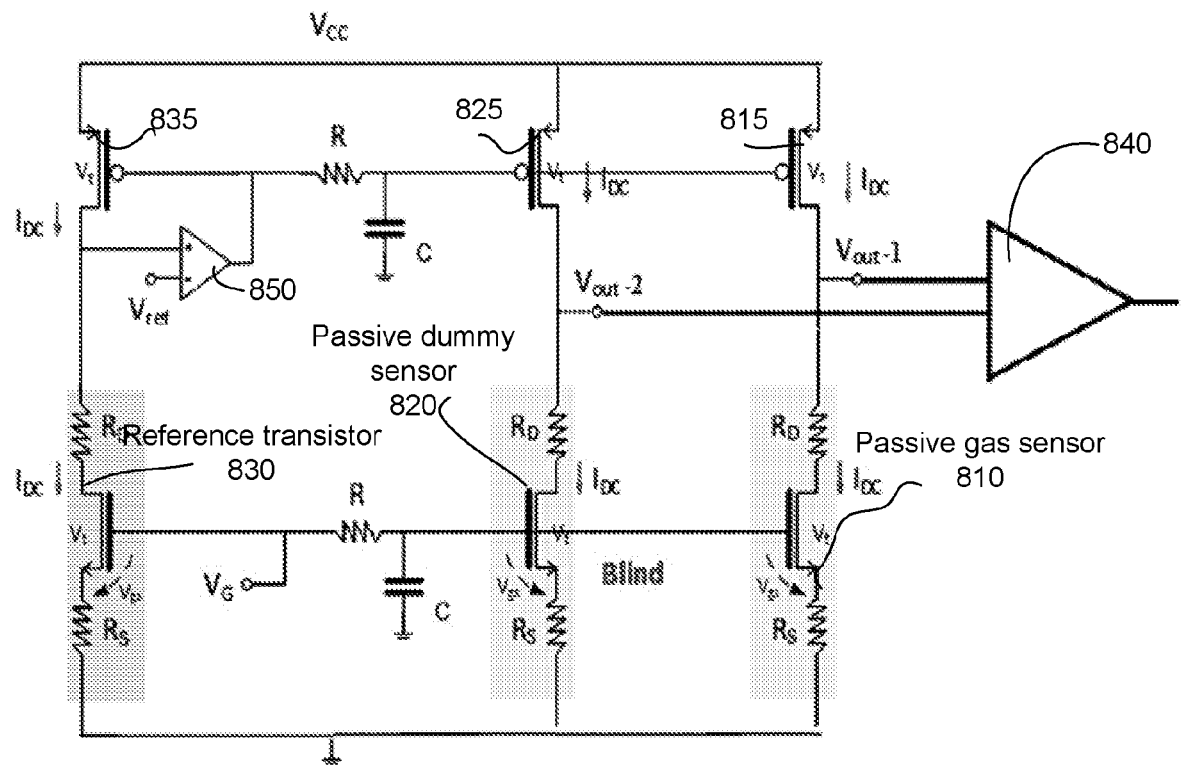
FIG. 8 illustrates a portion of a gas sensing device according to various embodiments of the invention.

FIG. 8 illustrates a portion of a gas sensing device according to various embodiments of the invention.

The portion includes a TMOS 810 that operates as a passive gas sensor, a TMOS 820 that operates as a passive dummy sensor, reference transistor 830, operational amplifier 850, transistors 815, 825 and 835 and differential amplifier 840.

TMOS 810 operates at subthreshold. The DC operation current $I_{DC}$ of the passive gas sensor is low. Still, the signal current (the passive gas sensor detection signal) is several orders of magnitude smaller than the DC current.

Accordingly, a bridge-like circuit is required to subtract the DC current as well as the effects of self-heating.

TMOS 820 may be identical to TMOS 810—but is shielded from the IR radiation by a mirror and hence cannot sense the wavelengths related to the gas that is being sensed.

The measurement of the gas is a voltage mode measurement—namely—the voltage between the input voltages of differential amplifier 840 (Vout1 and Vout2)

Reference transistor 830 and the RC circuit that follows the reference transistor 830 determine the (DC) gate-source voltage of TMOS 810 and TMOS 820.

Transistor 835 and operational amplifier 850 (fed by a reference voltage) determine the gate voltage of transistors 815 and 825—thereby determining the value of $I_{DC}$ fed from transistor 815 to TMOS 810 and the $I_{DC}$ fed from transistor 825 to TMOS 820—thereby determine the (DC) drain source voltage of TMOS 810 and TMOS 820.

This circuit enables to stabilize the operation point of the TMOSs of the passive gas sensor 810, passive dummy sensor 820—as they operate at subthreshold.

The TMOSs are implemented in MEMS and resistors $R_D$ and Rs are parasitic resistors Rs and Rd which reside on the holding arms of the MEMS TMOS pixels.

Other components may belong to the readout circuit or other non-MEMS components.

The whole circuit may be implemented as a MEMS sensor packaged in vacuum+an ASIC.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements.

The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A gas sensing device for sensing a certain gas that is associated with a certain spectral band, the gas sensing device comprises:
   a passive gas sensor that is configured to generate passive gas sensor detection signals that are responsive to the certain spectral band;
   a passive dummy sensor that is configured to generate passive dummy sensor detection signals that are indifferent to the certain spectral band; and
   at least one circuit that is configured to detect a presence or absence of the certain gas within a certain volume that is located within a field of view of the passive gas sensor and a field of view the passive dummy sensor based on a comparison between the passive gas sensor detection signals and the passive dummy sensor detection signals;

wherein a detection of the presence or absence of the certain gas within the certain volume is based on comparisons between passive gas sensor detection signals obtained during multiple measurements and passive dummy sensor detection signals obtained during the multiple measurements;

wherein the multiple measurements comprise a first measurement and a second measurement;

wherein the first measurement was taken when the gas sensing device was positioned at a first position (a) that is on a floor of a room and facing a ceiling and (b) in which the passive gas sensor has a first optical length;

wherein the second measurement was taken when the gas sensing device was positioned at a second position (a) that is on a head of a user and facing the ceiling, and (b) in which the passive gas sensor has a second optical length that differs by a known difference from the first optical length.

2. The gas sensing device according to claim 1 wherein the at least one circuit is configured to detect the presence or absence of the certain gas within the certain volume regardless of the optical length of each one of the passive gas sensor and the passive dummy sensor.

3. The gas sensing device according to claim 1 wherein the at least one circuit is configured to detect the presence or absence of the certain gas within the certain volume based on an optical length of each one of the passive gas sensor and the passive dummy sensor.

4. The gas sensing device according to claim 3 wherein the at least one circuit is configured to receive information about the optical length.

5. The gas sensing device according to claim 1 wherein the at least one circuit is configured to detect the presence or absence of the certain gas within the certain volume based, at least on ambient temperatures.

6. The gas sensing device according to claim 1 wherein the at least one circuit is configured to detect the presence or the absence of the certain gas within the certain volume based on the known difference, a first difference between passive gas sensor detection signals obtained during the first measurement and passive dummy sensor detection signals obtained during the first measurement, and a second difference between passive gas sensor detection signals obtained during the second measurement and passive dummy sensor detection signals obtained during the second measurement.

7. The gas sensing device according to claim 6 wherein the at least one circuit is configured to detect the presence or the absence of the certain gas within the certain volume based on an absolute value of a ratio between the second difference and the first difference.

8. The gas sensing device according to claim 7 wherein the at least one circuit is configured to detect a concentration of the certain gas within the certain volume by: dividing (a) the absolute value of the ratio between the second difference and the first difference, by (b) a product of the known difference multiplied by a gas absorption coefficient of the certain gas at a wavelength of detection of the passive gas sensor.

9. The gas sensing device according to claim 1 wherein the at least one circuit comprises a man machine interface for outputting instructing for positioning the gas sensing device at the first position and for outputting instructions for positioning the gas sensing device at the second position.

10. The gas sensing device according to claim 1 wherein the at least one circuit s configured to calculate the second position.

11. The gas sensing device according to claim 1 wherein the gas sensing device is a smartphone.

12. A method for sensing a certain gas that is associated with a certain spectral band, the method comprises:
generating, by a passive gas sensor of a gas sensing device, passive gas sensor detection signals that are responsive to the certain spectral band;
generating, by a passive dummy sensor of a gas sensing device, passive dummy sensor detection signals that are indifferent to the certain spectral band; and
detecting, by at least one circuit, a presence or absence of the certain gas within a certain volume that is located within a field of view of the passive gas sensor and a field of view of the passive dummy sensor based on a comparison between the passive gas sensor detection signals and the passive dummy sensor detection signals;
wherein the detecting of the presence or absence of the certain gas within the certain volume is based on comparisons between passive gas sensor detection signals obtained during multiple measurements and passive dummy sensor detection signals obtained during the multiple measurements;
wherein the multiple measurements comprise a first measurement and a second measurement;
wherein the first measurement was taken when the gas sensing device was positioned at a first position (a) that is on a floor of a room and facing a ceiling and (b) in which the passive gas sensor has a first optical length;
wherein the second measurement was taken when the gas sensing device was positioned at a second position (a) that is on a head of a user and facing the ceiling, and (b) in which the passive gas sensor has a second optical length that differs by a known difference from the first optical length.

13. The method according to claim 12 comprising detecting the presence or absence of the certain gas within the certain volume regardless of the optical length of each one of the passive gas sensor and the passive dummy sensor.

14. The method according to claim 12 comprising detecting the presence or absence of the certain gas within the certain volume based on an optical length of each one of the passive gas sensor and the passive dummy sensor.

15. The method according to claim 14 comprising receiving information about the optical length.

16. The method according to claim 12 comprising detecting the presence or absence of the certain gas within the certain volume based, at least on ambient temperatures.

17. The method according to claim 12 comprising detecting the presence or the absence of the certain gas within the certain volume based on the known difference, a first difference between passive gas sensor detection signals obtained during the first measurement and passive dummy sensor detection signals obtained during the first measurement, and a second difference between passive gas sensor detection signals obtained during the second measurement and passive dummy sensor detection signals obtained during the second measurement.

18. The method according to claim 17 comprising detecting the presence or the absence of the certain gas within the certain volume based on an absolute value of a ratio between the second difference and the first difference.

19. The method according to claim 18 comprising detecting a concentration of the certain gas within the certain volume by: dividing (a) the absolute value of the ratio between the second difference and the first difference, by (b) a product of the known difference multiplied by a gas absorption coefficient of the certain gas at a wavelength of detection of the passive gas sensor.

20. The method according to claim 12 comprising outputting instructions for positioning the gas sensing device at the first position and for outputting instructions for positioning the gas sensing device at the second position.

21. The method according to claim 12 comprising calculating the second position.

22. The method according to claim 12 wherein the gas sensing device is a smartphone.

* * * * *